(12) United States Patent
Sinusas et al.

(10) Patent No.: US 10,524,864 B2
(45) Date of Patent: Jan. 7, 2020

(54) REAL-TIME MOLECULAR IMAGING AND MINIMALLY-INVASIVE DETECTION IN INTERVENTIONAL CARDIOLOGY

(71) Applicants: Albert J. Sinusas, New Haven, CT (US); Farhad Daghighian, Hawthorne, CA (US)

(72) Inventors: Albert J. Sinusas, New Haven, CT (US); Farhad Daghighian, Hawthorne, CA (US)

(*) Notice: Subject to any disclaimer, the term of this patent is extended or adjusted under 35 U.S.C. 154(b) by 585 days.

(21) Appl. No.: 15/239,757

(22) Filed: Aug. 17, 2016

(65) Prior Publication Data
US 2017/0049518 A1     Feb. 23, 2017

Related U.S. Application Data

(60) Provisional application No. 62/206,172, filed on Aug. 17, 2015.

(51) Int. Cl.
| | |
|---|---|
| *A61M 31/00* | (2006.01) |
| *A61B 34/20* | (2016.01) |
| *A61B 18/14* | (2006.01) |
| *A61B 5/042* | (2006.01) |
| *A61B 6/00* | (2006.01) |
| *A61B 1/04* | (2006.01) |
| *A61B 1/018* | (2006.01) |
| *A61B 18/00* | (2006.01) |

(Continued)

(52) U.S. Cl.
CPC ............ *A61B 34/20* (2016.02); *A61B 5/0422* (2013.01); *A61B 18/1477* (2013.01); *A61B 18/1492* (2013.01); *A61B 1/018* (2013.01); *A61B 1/043* (2013.01); *A61B 6/4258* (2013.01); *A61B 6/481* (2013.01); *A61B 2010/045* (2013.01); *A61B 2018/00357* (2013.01); *A61B 2018/00904* (2013.01); *A61B 2034/2051* (2016.02); *A61B 2034/2072* (2016.02); *A61B 2090/3966* (2016.02)

(58) Field of Classification Search
CPC ............ A61B 18/1477; A61B 18/1492; A61B 5/0422; A61B 6/4258; A61B 6/481; A61B 2018/00904; A61B 5/0084; A61M 25/0026; A61M 25/0108; A61M 25/0082
See application file for complete search history.

(56) References Cited

U.S. PATENT DOCUMENTS

| | | | | |
|---|---|---|---|---|
| 5,336,222 A | * | 8/1994 | Durgin, Jr. ......... | A61B 18/1477 604/21 |
| 2002/0168317 A1 | * | 11/2002 | Daighighian ......... | A61K 49/18 424/1.11 |

(Continued)

*Primary Examiner* — Rebecca E Eisenberg
(74) *Attorney, Agent, or Firm* — M.J. Ram and Associates; Michael J. Ram (57) ABSTRACT

A catheter is disclosed for locating radiation tagged tissue within a mammalian body and treating tagged tissue or untagged tissue adjacent to the tagged tissue in a single procedure. The catheter includes in or on a distal end thereof one or more detectors for locating labeled tissue. A lumen extending from a proximal end of said tube to the distal end of said tube, includes a retractable and extendable needle positioned adjacent the distal end of said tube for delivering a liquid treatment modality. I the alternative the injector for delivering the treatment modality may be placed adjacent to the catheter for delivery of the treatment.

9 Claims, 9 Drawing Sheets

(51) Int. Cl.
*A61B 90/00* (2016.01)
*A61B 10/04* (2006.01)

(56) References Cited

U.S. PATENT DOCUMENTS

2004/0220461 A1* 11/2004 Schwartz .............. A61B 5/0422
                                                    600/374
2017/0007324 A1*  1/2017 Kadamus .............. A61M 25/04
2018/0070982 A1*  3/2018 Kimmel ............. A61B 17/3478

* cited by examiner fig. 1A  fig. 1B fig. 2A  fig. 2B fig. 3A  fig. 3B

REAL-TIME MOLECULAR IMAGING AND MINIMALLY-INVASIVE DETECTION IN INTERVENTIONAL CARDIOLOGY

The present application claims the benefit of U.S. Provisional Application No. 62/206,172, filed on Aug. 17, 2015.

BACKGROUND

There are several radioactive-labeled pharmaceuticals that preferentially accumulate in focal regions of normal and/or dysfunctional myocardium and associated neurovascular bundles within the atrial and ventricular chambers of the heart. These pharmaceuticals or other similarly labeled compounds can be used to mark the normal or abnormal tissue, depending on the characteristics of those labeled compounds, for subsequent delivery of treatment modalities directly to those marked tissue.

Examples of these radiopharmaceuticals are:
  a. C-11, F-18, or Tc-99m labeled annexin-V accumulates in apoptotic cells of the vasculature and myocardium.
  b. Radiolabeled Matrix metalloproteinase (MMP) inhibitor, preferentially accumulates in the regions of the myocardium involved in myocardial and vascular injury and fibrosis and repair associated with atrial and ventricular remodeling and have been associated with risk for atrial or ventricular arrhythmias. Radiolabeled In particular, matrix metalloproteinase (MMP) inhibitor, accumulates in myocardial fibrosis. In some embodiments, the MMP inhibitor has an inhibitory constant (Ki) of <1000 nM; in other embodiments, the MMP inhibitor can have an inhibitory constant Ki of <100 nM. Further, in some embodiments, the MMP inhibitor can be an inhibitor of one or more matrix metalloproteinases selected from the group consisting of MMP-2, MMP-9 and MMP-14.

Fluorodeoxyglucose (18F) (FDG), or fludeoxyglucose F 18 (USAN and USP), also commonly called fluorodeoxyglucose and abbreviated [18F]FDG, 18F-FDG or FDG is a radiopharmaceutical used in the medical imaging modality positron emission tomography (PET). 18F FDG accumulates in inflammatory cells associated with myocardial reperfusion injury following myocardial injury or stress-induced ischemia, or other inflammatory myo-cellular processes within the heart (sarcoidosis, myocarditis), particularly under fasting conditions when myocardial glucose uptake is suppressed. ("The Use of 18F-FDG PET in the Diagnosis of Cardiac Sarcoidosis: A Systematic Review and Metaanalysis Including the Ontario Experience"; George Youssef et al. *J Nucl Med* (2012); 53:241-248).

Re-186 or Re-188 labeled RDG are also good candidates for infarct imaging.

Thomas Klein et al., using non-invasive external gamma camera imaging, studied three-dimensional 123I-Meta-Iodobenzylguanidine (1-123 labeled mIBG) cardiac innervation maps to assess substrate and successful ablate sites for ventricular tachycardia (VT); (*Circ Arrhythmia Electrophysiol.* (2015); 8:583-591). He demonstrated that 123I-mIBG innervation defects are larger than bipolar voltage-defined scar and cannot be detected with standard voltage criteria. Thirty-six percent of successful VT ablation sites demonstrated normal voltages (>1.5 mV), but all ablation sites were within the areas of abnormal innervation. 123I-mIBG innervation maps may provide critical information about triggers/substrate modifiers and could improve understanding of VT substrate and facilitate VT ablation.

However, the prior art does not describe or suggest using a detection catheter such as described below to locate the radiation labeled tissue. A beta emitting isotope of iodine, such as 1-124 or 1-131 can be used to label mIBG and the detector catheter as described below can be used to locate the areas of abnormal innervation tagged with the labeled mIBG and then deliver therapy (e.g.; ablation, treatment drugs, cells, etc.) can be delivered directly to the radiation tagged tissue in real time.

Examples of such radiopharmaceuticals that preferentially accumulate in normal myocardium are:
  a. Thallium-201, rubidium-82, N-13 NH3, O-15 or O-14 labeled $H_2O$, and Tc-99m labeled sestamibi and tetrofosmin each accumulate in myocardium with normal blood perfusion, and demonstrate no or reduced uptake in ischemic myocardium under stress or in the presence of myocardial infarction.
  b. F-18 FDG is also known to accumulate in normal, viable and hibernating myocardium, in the presence of glucose and insulin, and have no or reduced uptake in chronically infarcted tissues under these conditions
  c. F-18 LMI1195 or other beta-emitting agents that bind to sympathetic presynaptic and post-synaptic receptors, and accumulate in ganglionic complexes within the heart are predictive of risk for heart failure, arrhythmias, and sudden cardiac death and can be used to guide selective ablation of ganglionic complexes within the heart reducing the risk for arrhythmias. For example, 1-124 or 1-131 labeled MIBG may also be used.

The distribution of such radiopharmaceuticals is readily imaged in the heart using gamma cameras or PET scanners.

Another way of mapping the distribution of radioactivity in an organ is by scanning it with a radiation detection probe. These probes can have single or multiple detectors. These detector probes can be sensitive to gamma rays, beta rays, alpha rays or a combination of these radiations, as well as a selective energy window of these radiations. These probes can also be combined with position sensors (electromagnetic, optical or mechanical), as well as with detectors and cameras of other types of radiations such infra-red, visible light, ultraviolet, or ultrasound.

Method of Delivery of Therapy to Myocardium

The percutaneous delivery of therapies to the myocardium (endocardial surface of atria or ventricles) with directable catheters has become part of routine clinical practice. These catheter-based deliver systems can be guided in the heart based on 2-dimensional or 3-dimensional anatomic locations determined either by external imaging, magnetic field localization using electrode catheters, or electro anatomical mapping of the surface of the heart. These minimally invasive catheter-based systems can deliver a wide range of different types of therapy, including delivery of radiofrequency energy or thermal energy (hot or cold) for ablation of tissues or intramyocardial injection of therapeutic materials. However, the therapeutic delivery of these agents in combination with a diagnostic radio labeled tracer detector probe to locate and pinpoint the specific site for delivery of the therapeutic materials has not been shown or possible in the past. Some more specific examples are outlined below.

Ablation of arrhythmia-generating areas of the myocardium is usually achieved by placing electrodes inside the heart minimally invasively, and pacing the heart until the arrhythmia is induced which is sometimes dangerous. The network of electrodes inside the heart then localize the area that needs ablation which can be performed by local delivery of radiofrequency energy, thermal energy, or cell toxic materials like ethanol.

Ischemic heart disease (IHD) remains a major healthcare issue in the United States, and often results in myocardial infarction (MI) and adverse post-MI LV remodeling, which manifests as changes in LV structure, volume, geometry, and function. An estimated eight million people are afflicted with MI in the United States with around 610,000 new cases reported each year. (Lloyd-Jones D, Adams R J, Brown $T_M$, Camethon M, Dai S, De Simone G, Ferguson T B, Ford E, Furie K and Gillespie C. "Heart disease and stroke statistics-2010 update A report from the American Heart Association". Circulation, 2010; 121:e46-e215; Go A S, Mozaffarian D, Roger V L, Benjamin E J, Berry J D, Blaha M J, Dai S, Ford E S, Fox C S, Franco S, Fullerton H J, Gillespie C, Hailpem S M, Heit J A, Howard V J, Huffman M D, Judd S E, Kissela B M, Kittner S J, Lackland D T, Lichtman J H, Lisabeth L D, Mackey R H, Magid D J, Marcus G M, Marelli A, Matchar D B, McGuire D K, Mohler E R, 3rd, Moy C S, Mussolino M E, Neumar R W, Nichol G, Pandey D K, Paynter N P, Reeves M J, Sorlie P D, Stein J, Towfighi A, Turan T N, Virani S S, Wong N D, Woo D, Tumer M B, "American Heart Association Statistics C and Stroke Statistics S. Heart disease and stroke statistics—2014 update: a report from the American Heart Association", Circulation. 2014; 129:e28-e292) The rate and degree of post-MI LV remodeling has been clearly implicated as independent predictors of morbidity, complicating congestive heart failure (CHF), and mortality. The life threatening complications of MI are associated with significant health care costs. The annual medical cost of recurrent MI is approximately $2.4 billion (B), while the annual costs associated with heart failure (1.1 M hospitalizations) exceeds $30.1 B. It is estimated that by 2030 the total cost will increase to nearly $70 B. MI is the leading cause of CHF, which accounts for 35% of all cardiovascular deaths. Post-MI remodeling can be modulated by pharmacological therapy, cellular transplantation, as well as the administration of therapeutic biomaterials. Therefore, these therapeutic approaches that reduce post-MI remodeling will have a major impact on growing health care costs associated with MI and complication CHF.

Over the past decade, cell therapy has emerged as a promising treatment strategy, with a goal of implanting live cells in the infarcted region. Multiple cell types including bone marrow mononuclear cells, bone marrow mesenchymal cells, and adipose tissue-derived cells have been used in acute or convalescent MI, but efficacy has been inconsistent and limited. These cells can be injected into myocardium during surgical procedures, delivered percutaneously via catheters, or delivered antigrade by intracoronary infusion or retrograde through the coronary sinus in patients with ischemic or non-ischemic cardiomyopathy.

Recent clinical trials have demonstrated improved efficacy when cells for treatment are injected directly into the heart tissue either during surgical procedures or percutaneously. This direct delivery results in better retention of cells as reported by Anthony Mathur et. al. in a 2015 review in Circulation Research (Fisher S A, Doree C, Mathur A et al. (2015). "Meta-analysis of cell therapy trials for patients with heart failure". Circulation Research, 116, (8) 1361-1377.

As an alternative, therapeutic delivery of genes to the heart via direct injection or via intracoronary injection has been demonstrated. (S. R. Eckhouse, B. P. Purcell, J. R. McGarvey, D. Lobb, C. B. Logdon, H. Doviak, J. W. O'Neil, J. A. Schuman, C. P. Novak, K. N. Zellars, S. Pettaway, R. A. Black, A. Khakoo, T. Lee, R. Mukherjee, J. H. Gorman, R. C. Gorman, R. A. Black, J. A. Burdick, F. G. Spinale, "Local Hydrogel Release of Recombinant TIMP-3 Attenuates Adverse Left Ventricular Remodeling after Experimental", Science Translational Medicine, 6:223ra21, 2014; Brendan P. Purcell D L, Manoj B. Charati, Shauna M. Dorsey, Ryan J. Wade, Kia N. Zellars, Heather Doviak, Sara Pettaway, Christina B. Logdon, James A. Shuman, Parker D. Freels, Joseph H. GormanIII, Robert C. Gorman, Francis G. Spinale and Jason A. Burdick. "Injectable And Bioresponsive Hydrogels For On-Demand Matrix Metalloproteinase Inhibition" Nature Materials (2014); 13; Burdick J A and Prestwich G D. "Hyaluronic Acid Hydrogels For Biomedical Applications", Adv Mater. (2011); 23:H41-56; Ifkovits J L, Tous E, Minakawa M, Morita M, Robb J D, Koomalsingh K J, Gorman J H, 3rd, Gorman R C and Burdick J A. "Injectable Hydrogel Properties Influence Infarct Expansion And Extent Of Postinfarction Left Ventricular Remodeling In An Ovine Model", Proc Natl Acad Sci USA (2010); 107:11507-12; Tous E, Ifkovits J L, Koomalsingh K J, Shuto T, Soeda T, Kondo N, Gorman III J H, Gorman R C and Burdick J A. "Influence Of Injectable Hyaluronic Acid Hydrogel Degradation Behavior On Infarction-Induced Ventricular Remodeling. Biomacromolecules. (2011); 12:4127-4135; Eckhouse S R, Purcell B P, McGarvey J R, Lobb D, Logdon C B, Doviak H, O'Neill J W, Shuman J A, Novack C P, Zellars K N, Pettaway S, Black R A, Khakoo A, Lee T, Mukherjee R, Gorman J H, Gorman R C, Burdick J A and Spinale F G. "Local Hydrogel Release Of Recombinant TIMP-3 Attenuates Adverse Left Ventricular Remodeling After Experimental Myocardial Infarction". Sci Transl Med. (2014); 6:223ra21; Thorn S, Stacy M R, Purcell B P, Doviak H, Shuman J, Juarez Perez E, Burdick J, FG Spinale and AJ Sinusas. "In Vivo Non-Invasive Evaluation Of Therapeutic Hydrogels For Modulation Of Post Infarction Remodeling: Role Of MMP-Targeted SPECT Myocardial Imaging In A Chronic Porcine Model", European Heart Journal-Cardiovascular Imaging. (2015); 16; Purcell B P, Lobb D, Charati M B, Dorsey S M, Wade R J, Zellars K N, Doviak H, Pettaway S, Logdon C B, Shuman J A, Freels P D, Gorman J H, 3rd, Gorman R C, Spinale F G and Burdick J A. "Injectable And Bioresponsive Hydrogels For On-Demand Matrix Metalloproteinase Inhibition", Nat Mater. 2014; 13:653-61.

Many radioisotopes, in addition to gamma rays, emit electrons or positrons (beta rays). Gamma rays travel several centimeters in tissue. Therefore, a detector sensitive to gamma rays will be susceptible to spurious gamma rays emitted by distant organs and background tissue. This background radiation could result in mis-location of small lesions. Beta rays travel just a few millimeters, and therefore a beta ray detector has the advantage of sensing only the local radioactive concentration.

One limitation of gamma probes is their inability to distinguish between the signal and the background radioactivity which obscures small lesions with low tumor/background uptake ratios. The beta probe was invented to circumvent this limitation in traditional gamma probe technology. Since beta rays have short depth of penetration in tissue (~mm), a beta sensitive probe is not affected by the background radiation.

The Beta detector Probe is ideal for the detection of minute tagged tissue which, due to the short penetration range of beta rays in tissue, is not obscured by the radioactivity accumulated in normal tissues. In an experiment utilizing prostate cancer cells and antibody labeled with I-131, the beta probe was capable of detecting 0.06 g of tumor in presence of 2 mCi of background.

The first intra-operative beta probe was described in U.S. Pat. No. 5,008,546, Daghighian et. al. Intraoperative Beta Probe and Method of Using the Same, and its use is described in F. Daghighian, J. C. Mazziotta, E. J. Hoffman, P. Shenderov, B. Eshaghian, S. Siegel, and M. E. Phelps. "Intraoperative Beta Probe: A Device For Detecting Tissue Labeled With Positron Or Electron Emitting Isotopes During Surgery.". *Medical Physics,* 21. No. 1, pp. 153-157, (Jan. 1994) See also R. R. Raylman. "Performance Of A Dual, Solid-State Intraoperative Probe System With 18F, 99mtc, And (111)In.". *Journal of Nuclear Medicine: Society of Nuclear Medicine,* 42, No. 2, pp. 352-360, (Feb. 2001) and V. E. Strong, J. Humm, P. Russo, A. Jungbluth, W. D. Wong, F. Daghighian, L. Old, Y. Fong, S. Larson. "A Novel Method To Localize Antibody-Targeted Cancer Deposits Intraoperatively Using Handheld PET Beta And Gamma Probes". *Surgical Endoscoov,* 22. p. 386-391, (Nov. 2007), each of which is incorporated herein in their entirety by reference.

The above referenced beta-sensitive probe utilizes a plastic scintillator which is relatively insensitive to gamma radiation (although a small amount is always detected). These spurious gamma rays may become significant when background radioactivity is high. To remedy this, a reference gamma ray detector can be placed near the beta detector for use in subtracting the background gamma rays from the radiation detected by the beta detector.

DESCRIPTION OF DRAWING

FIG. 1 B is a cutaway end view of the catheter of FIG. 1A.

DETAILED DESCRIPTION

Described herein is series of theranostic devices that feature a flexible, narrow gauge catheter with a retractable needle and, in some embodiments, a solid state beta detector capable of high sensitivity measurement of the radioactivity of the endocardial surface of tagged heart tissue. "Theranostic" is a term developed to describe treatment modalities which combine diagnostic and therapeutic capabilities into a single agent, such as a single device. Disclosed herein are hybrid catheter-based system that can be delivered percutaneously to detect molecularly-targeted radiotracer signals, for example on the endocardial surface, and in such an instance direct intramyocardial delivery of therapeutics using molecular or radiotracer guidance to maximize treatment benefits. One potential application of this technology is the intramyocardial delivery of therapeutics (e.g. stem cells, transnostic polymers, etc.) to injured myocardium following myocardial infarction.

A radiation-detection catheter can be used to enter the chambers of the heart in a minimally-invasive taken up by the tissue of the myocardial surface, or structures immediately adjacent thereto or into viable or dysfunctional heart tissue. Additionally, the catheter can contain a retractable needle connected to a flowable treatment source by a thin tube for delivery and injection of such therapeutic materials into the myocardium. These therapeutic materials can consist of cells, genes, polymers, inhibitory microRNAs, DNA, plasmids, chemicals, enzymes, growth factors, or a variety of medicinal compounds or combinations thereof. The intent of the devices and procedures shown and described herein is to provide a better means to locate tagged tissue, for example tissue tagged with a radioactive compounds, and to deliver a therapeutic composition directly to the vicinity of the tagged location in real time (in a single procedure), and is not intended to be limited by the method of tagging or the tissue treatment modality. It should be noted that tissue tagging is not limited to radiation tagging and other modalities, such as tagging with fluorescent or phosphorescent compounds can be used in conjunction with optical visualization techniques. Further, while the examples set forth herein are directed to the delivery of therapeutic material to the heart, the catheter described herein is not limited to therapeutic delivery to heart tissue and is contemplated to be useful to deliver therapeutic compositions to any tissue or organ in the body which can be reached by a catheter or similar tubular device including, but not limited to, the intestinal tract, bladder, kidney, liver, brain, lungs, etc.

In a first embodiment, the catheter contains one or more electrodes that detect the electrical signals of the myocardium and help localization during electrophysiology.

In another embodiment the catheter also contains a detector that is preferentially sensitive to beta rays.

In a further embodiment, the catheter also contains a detector that is sensitive to gamma rays and/or x-rays.

In a still further embodiment, the catheter also contains two detectors in tandem, one for detection of beta rays and the other for detection of gamma and/or x-rays.

In still further embodiment, the catheter can also include light detectors, electrodes and/or lasers, the electrodes suitable for detecting electrical activity or delivering an electrical pulse or stimulus.

In still further embodiment, the catheter can also include a biopsy needle or other means for removing a small piece of the myocardial tissue.

In still further embodiment, the catheter can also include means to deliver RF or cryo-ablation.

Figure 1A:
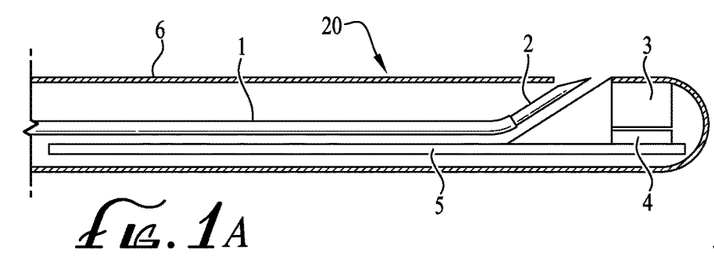
FIG. 1A is a cut-away side view of a first embodiment of a radiation detection catheter incorporating features of the invention showing a needle in a stored position and including a plastic scintillator coupled to a solid state photomultiplier.
Figure 1B:
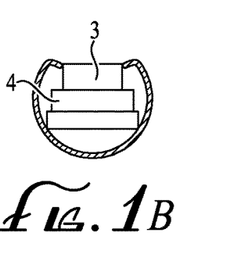

FIG. 1A shows the tip and distal end of a catheter 20 with side viewing capability. FIG. 1 B is a cut-away end view of the same catheter The catheter contains a hollow conduit, preferably a micro plastic tube 1, such as a Tygon® plastic tube, that is connected to a needle 2 (for example a 30 gauge needle). The detector comprises a plastic scintillator 3 connected to a solid state photomultiplier 4. A plastic scintillator is preferred due to its selective sensitivity to beta rays and insensitivity to gamma rays.

Figure 2A:
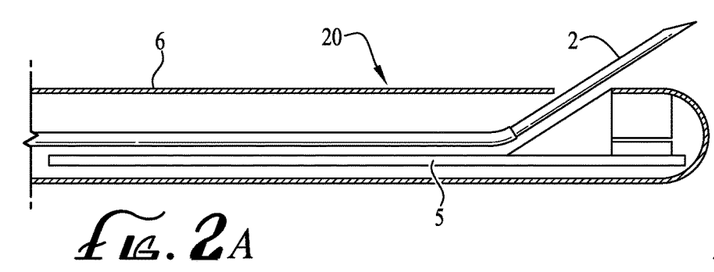
FIG. 2A is a cut-away side view of the radiation detection catheter embodiment of FIG. 1A with the needle in an extended orientation incorporating features of the invention.
Figure 2B:
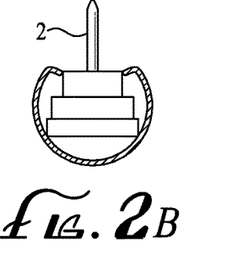
FIG. 2B is a cutaway end view of the catheter of FIG. 2A.

FIGS. 2A and 2B illustrate the same catheter 20 as in FIGS. 1A and 1B with the needle 2 extended forward, as best shown in the front view, FIG. 2B. The outside jacket of the catheter 6 is stiff enough for guidance. However, if necessary, a guidewire can be used and the catheter can have an additional lumen for receiving the guidewire used to aid in placement of the catheter. Cables or electrical conduits 5 carry the signals from the detector to an outside monitor (not shown) for measurement, display and placement guidance.

Figure 3A:
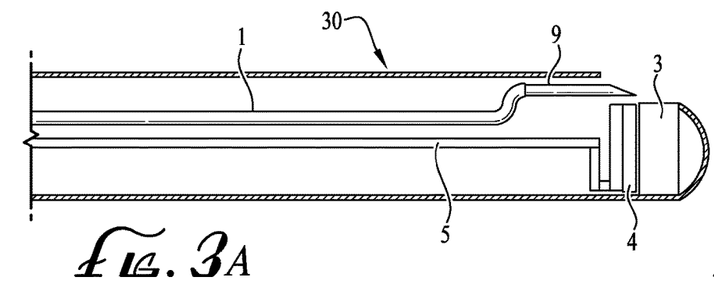
FIG. 3A is a cut-away side view of an embodiment of a radiation detection catheter incorporating features of the invention with a second, different shaped needle in a stored position, said catheter including a forward facing detector.
Figure 3B:
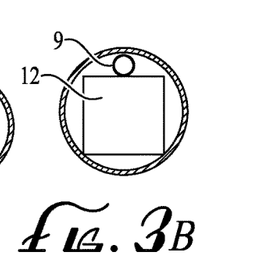
FIG. 3B is a cutaway end view of the catheter of FIG. 3A.

FIGS. 3A and 3B show a catheter 30 with a front-viewing detector 12 mounted on the distal end thereof. The needle, or ablation tool 9 in its retracted position can be seen in the front view 3B. One skilled in the art will recognize that once the catheter is positioned adjacent the tissue to be treated the needle or ablation tool can be extended for injecting the treatment modality, or electrical or cryo ablation directly into the targeted tissue. Also shown is the tube 1 attached to the needle 9 that carries the treatment material for injection.

Figure 4A:
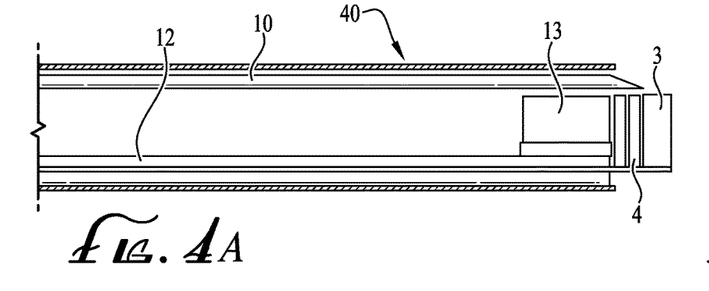
FIG. 4A is a cut-away side view of a third embodiment of a radiation detection catheter with two detectors, including a gamma or x-ray detector incorporating features of the invention with a third version of a needle in a stored view.
Figure 4B:
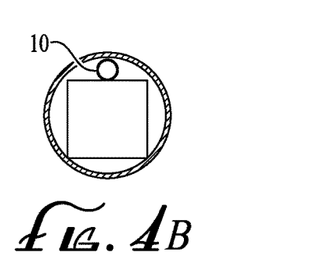
FIG. 4B is a cutaway end view of the catheter of FIG. 4A.

FIGS. 4A and 4B show a different needle or ablation tool arrangement comprising a straight needle or ablation tool in a dual detector catheter 40. A second detector 13 sensitive to gamma or x-rays is connected to a multi-wire cable 12. Once the labeled tissue 106, 113, 123, 144 (see FIGS. 10, 11, 13 and 16) is located the needle or the ablation tools can be extended to inject the treatment material into the labeled tissue or deliver electrical or cryo ablation.

Figure 5A:
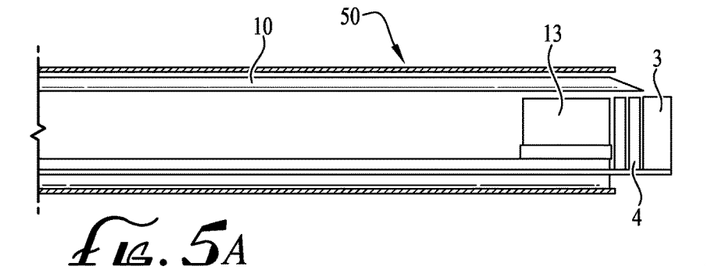
FIG. 5A is a cut-away side view of a fourth embodiment of a radiation detection catheter including a gamma or x-ray detector and a position sensor incorporating features of the invention with the third version of the needle in a stored view.
Figure 5B:
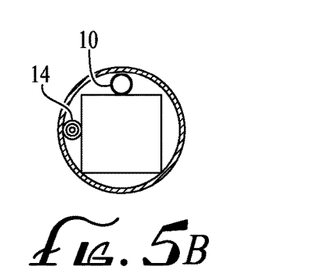
FIG. 5B is a cutaway end view of the catheter of FIG. 5A.

FIGS. 5A and 5B show a catheter 50 containing fiber optics 14 that is capable of detecting luminescence light emitted by a tracer that was injected into the tissue or systemically delivered and preferentially absorbed by target tissue.

Figure 6A:
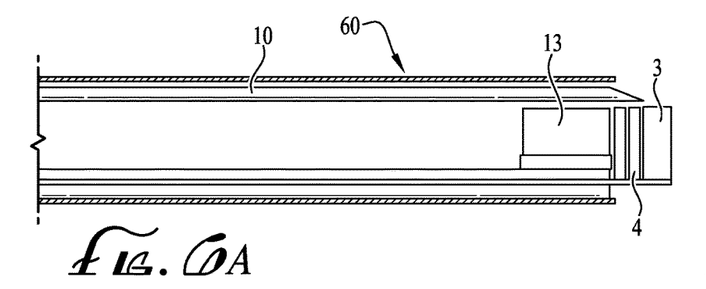
FIG. 6A is a cut-away side view of a fifth embodiment of a radiation detection catheter including a gamma or x-ray detector and a CCD camera incorporating features of the invention with the third version of the needle in a stored view.
Figure 6B:
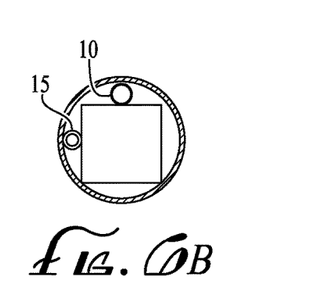
FIG. 6B is a cutaway end view of the catheter of FIG. 6A.

FIGS. 6A and 6B show a catheter 60 containing a small CCD camera 15 that is capable of detecting luminescence light emitted by a tracer that was injected into the tissue or, alternatively providing a visual image of targeted tissue.

Figure 7A:
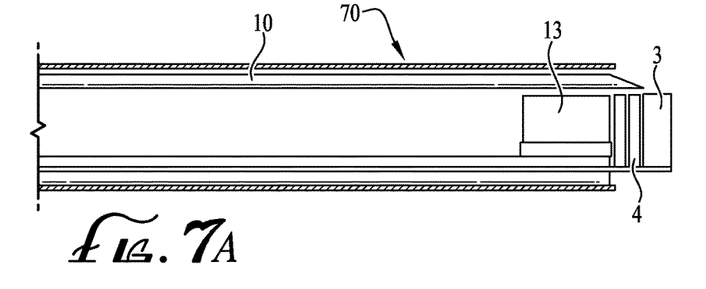
FIG. 7A is a cut-away side view of a sixth embodiment of a radiation detection catheter including a gamma or x-ray detector, an electrode and a laser incorporating features of the invention with the third version of the needle in a stored view.
Figure 7B:
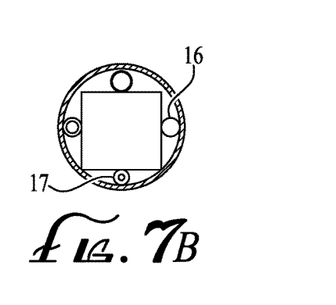
FIG. 7B is a cutaway end view of the catheter of FIG. 7A.

FIGS. 7A and 7B show a catheter 70 containing an electrode 16 for measurement of the electrical activity of the heart tissue, or delivering electrical stimulation to the heart, as well as a laser 17 to activate fluorescent compounds that can be injected, or otherwise placed, into the tissue. Alternatively, the laser can be used to deliver ionizing radiation to the tissue or to ablate the tissue surface.

Figure 8A:
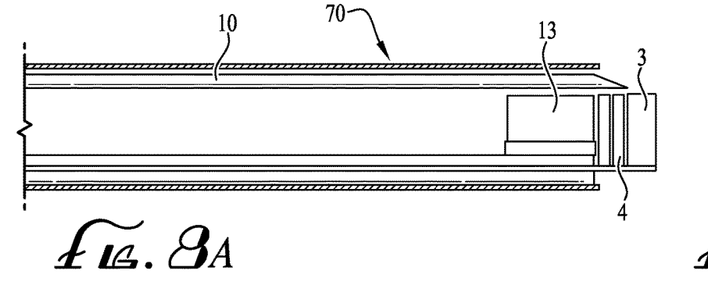
FIG. 8A is a cut-away side view of a further embodiment of a radiation detection catheter including a gamma or x-ray detector and further including an electrode for measuring heart electrical activity and a biopsy needle.
Figure 8B:
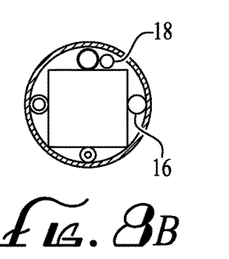
FIG. 8B is a cutaway end view of the catheter of FIG. 8A.

FIGS. 8A and 8B show a catheter 70 containing an electrode 16 for measurement of the electrical activity of the heart tissue, as well as an electromagnetic position sensor 18 to track the position of the catheter and correlate it to the position of other catheters or devices being used in the procedure.

Figure 9A:
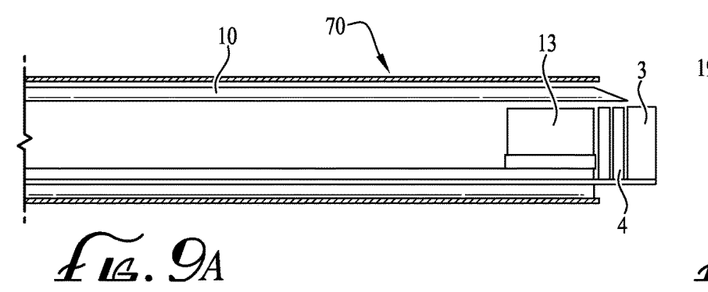
FIG. 9A is a cut-away side view of a further embodiment of a radiation detection catheter including two detectors, a needle for injection, a position sensor for tracking, a laser for photo-excitation, a biopsy port and an electrode for sensing and measuring heart electrical activity and devices for delivery of RF or cryo ablation.

FIG. 9 A is a cut-away side view of a further embodiment of a radiation detection catheter including two detectors, a needle for injection, position sensor for tracking, a laser for photo excitation, a biopsy port, an electrode for sensing electrical activity, and a mean for delivery of RF or cryo-ablation 19.

Figure 9B:
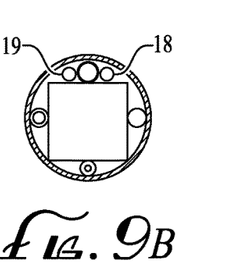
FIG. 9B is a cutaway end view of the catheter of FIG. 9A.

FIG. 9B is a cutaway end view of the catheter of FIG. 9A.

Figure 10:
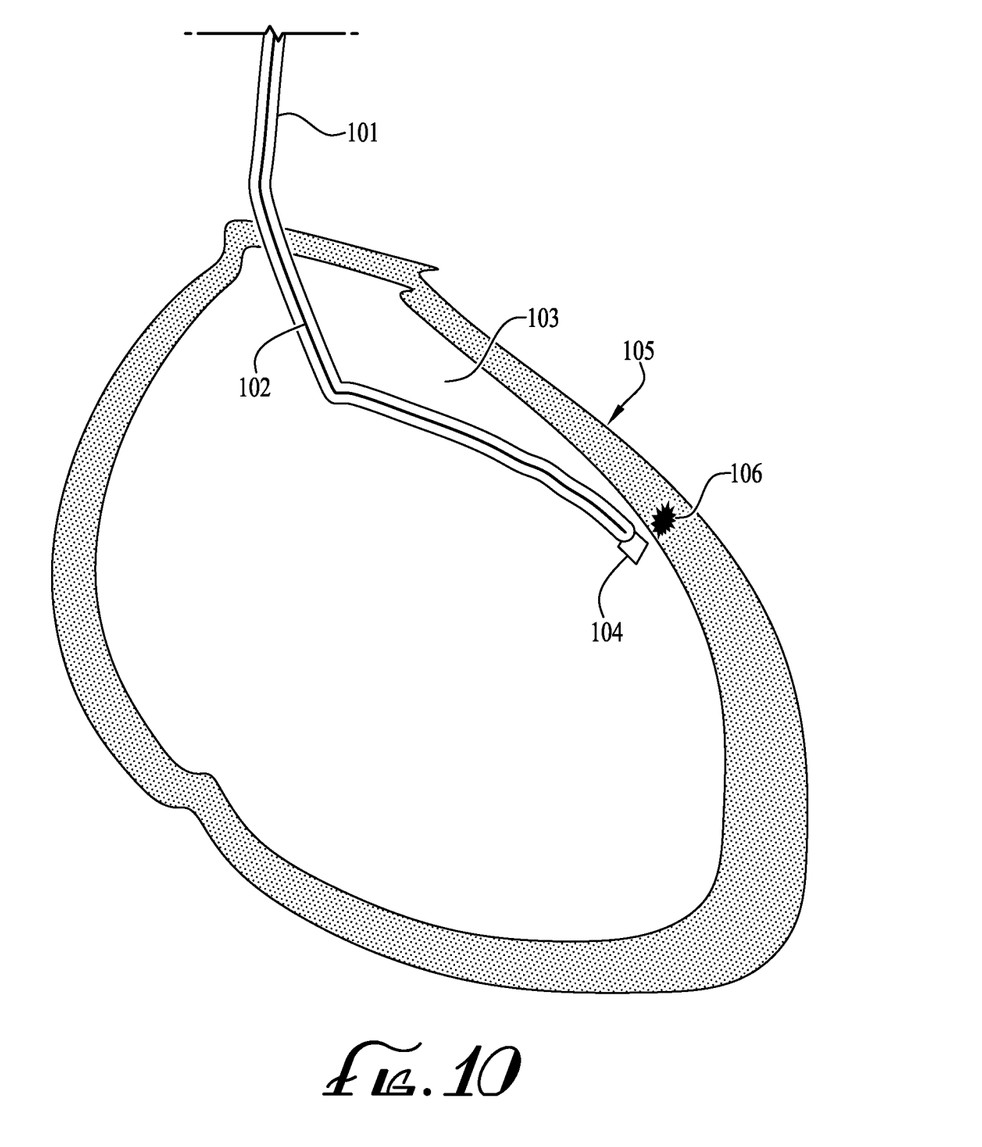
FIG. 10 shows a catheter incorporating features of the invention inside the ventricle of the heart.

FIG. 10 shows a detector-catheter 101 incorporating features of the invention positioned inside the left ventricle 103 of the heart 105. This detector catheter has one detector 104 and incorporates a tube and needle 102 for injecting medicinal compounds, therapeutic cells, or genetic material.

Figure 11:
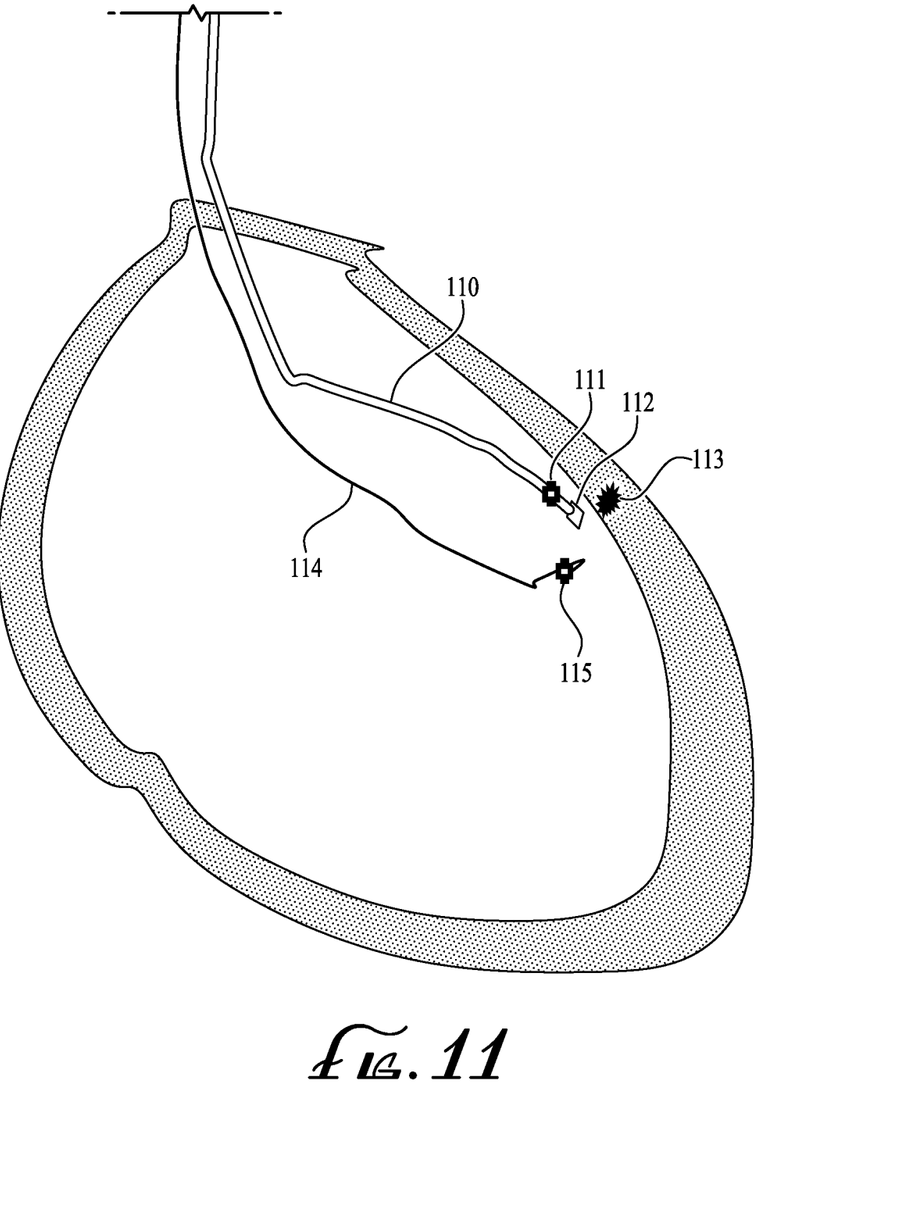
FIG. 11 shows a detector-catheter incorporating features of the invention inside the ventricle of the heart and a separate injection catheter.

FIG. 11 is a variation of the detector-catheter 110 and its position sensor 111 and detector 112, inside the left ventricle of the heart. The injection catheter or ablation tool 114 is not part of the detector 112 but is placed separately into the left ventricle so the operator has more control of the placement of location of the lesion 113, and injection or ablation procedures by utilizing the information provided by the position sensor 115.

Figures 12A, 12B:
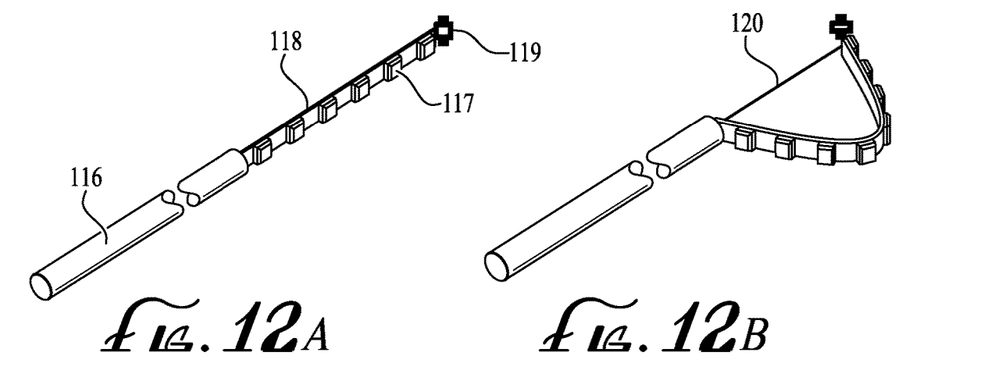
FIG. 12A shows a flexible beta camera on the distal end of a catheter.
FIG. 12B shows the beta camera on the end of a catheter curved into a form to match the shape of the inside wall of the myocardium.

FIG. 12A shows a 1-Dimensional beta camera 118 with radiation detectors 117 attached to the end of a placement catheter 116. A position sensor 119 is also shown.

FIG. 12B shows the 1-Dimensional beta camera 118 in a deployed position. The beta cameras are mounted on a flexible backing which can be bent to take the form of the myocardium inner wall by pulling on a cable 120 attached to the distal end of the flexible backing, the cable extending through the length of the placement catheter 116.

Figure 13:
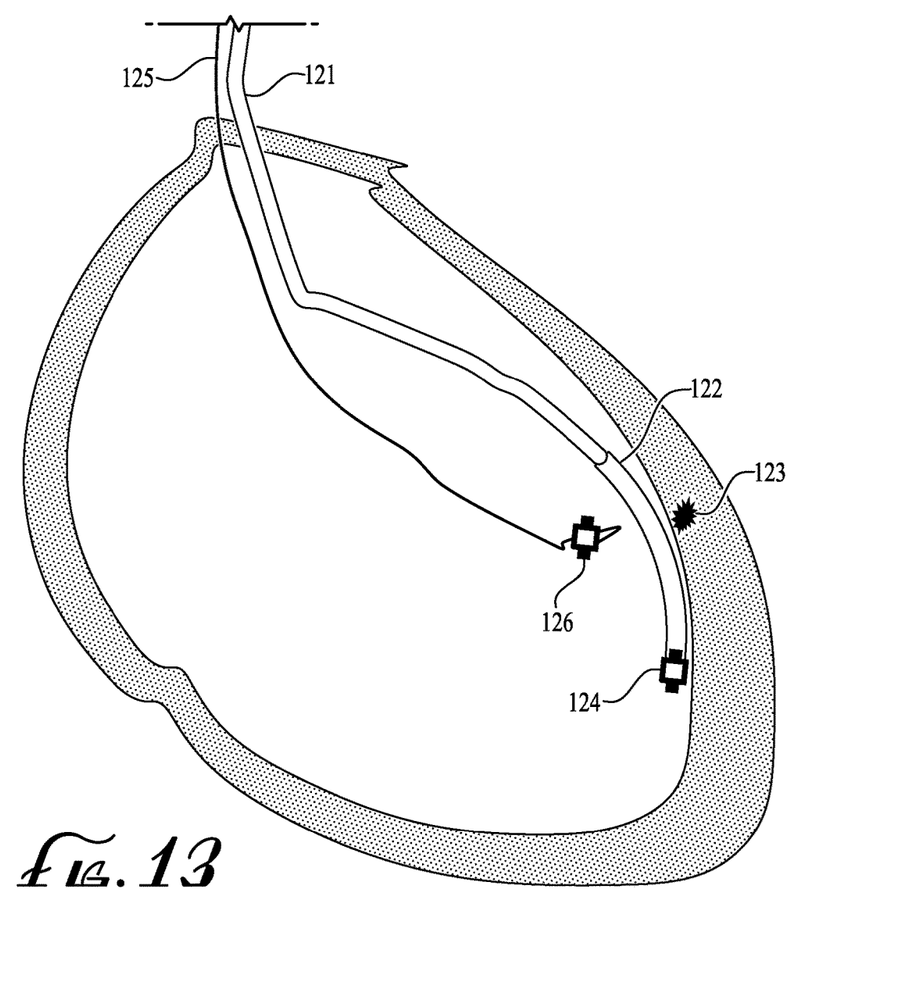
FIG. 13 illustrates the catheter tip with beta camera positioned within the heart with the beta camera curved to contact the interior wall of the heart, therapy delivering catheter or an injector or ablation device being separately introduced adjacent thereto.

FIG. 13 shows the 1-Dimensional beta camera 122 deployed into the heart, the flexible backing bent to conform to the myocardium inner wall in order to find the radiolabeled lesion 123. A position sensor 124 is attached to this beta camera. In FIG. 13 the injector or ablation tool 125 is shown as separate from the detector catheter with its position sensor 126.

Figure 14:
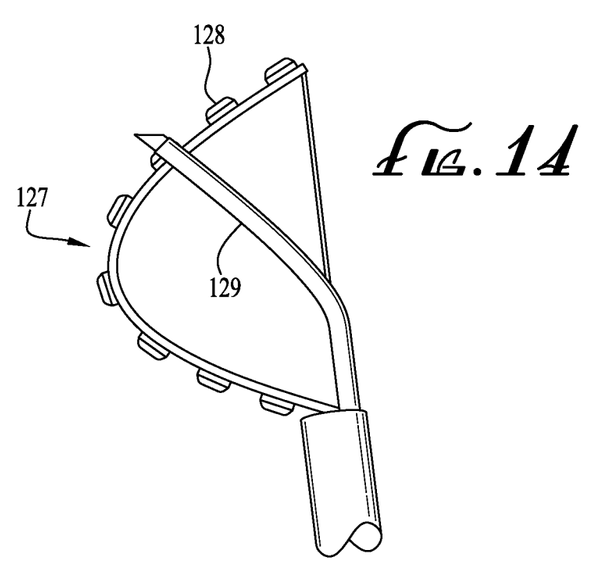
FIG. 14 illustrates the flexible beta camera in conformal apposition to the inside of the heart, and the needle positioned to deliver treatment material. Also illustrated is electrodes placed between each beta camera.

FIG. 14 shows a variation of the flexible 1-Dimensional beta camera 127 of FIGS. 12A and 12B with radiation detectors 128 and the injector needle or ablation tool 129 extending from a lumen in the delivery catheter. The device shown also includes position sensors 111, 115, 119, 124, 126 (see FIGS. 11, 12A, 13) on or adjacent to the beta camera or injection needle or ablation tool.

Figure 15:
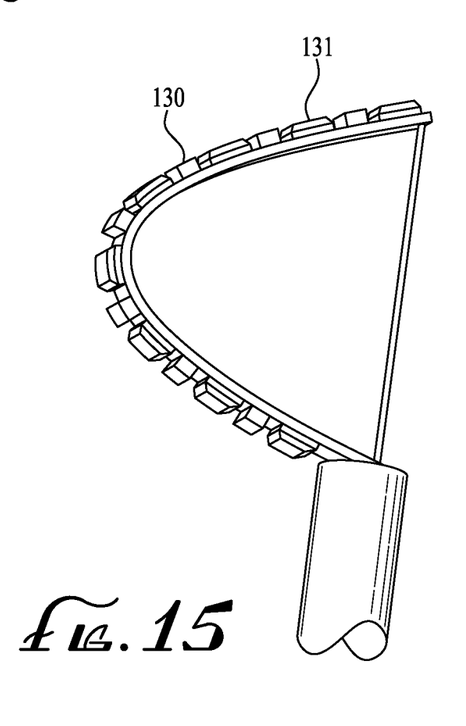
FIG. 15 is an enlarged view of the distal end of the delivery catheter with alternating electrodes and beta cameras.

FIG. 15 is an enlarged view of the distal end of the placement catheter with the 1-Dimensional beta camera in its bent configuration, with electrodes 130 positioned between each radiation detector 131 for mapping electrical activity of the heart or delivering ablation.

Figure 16:
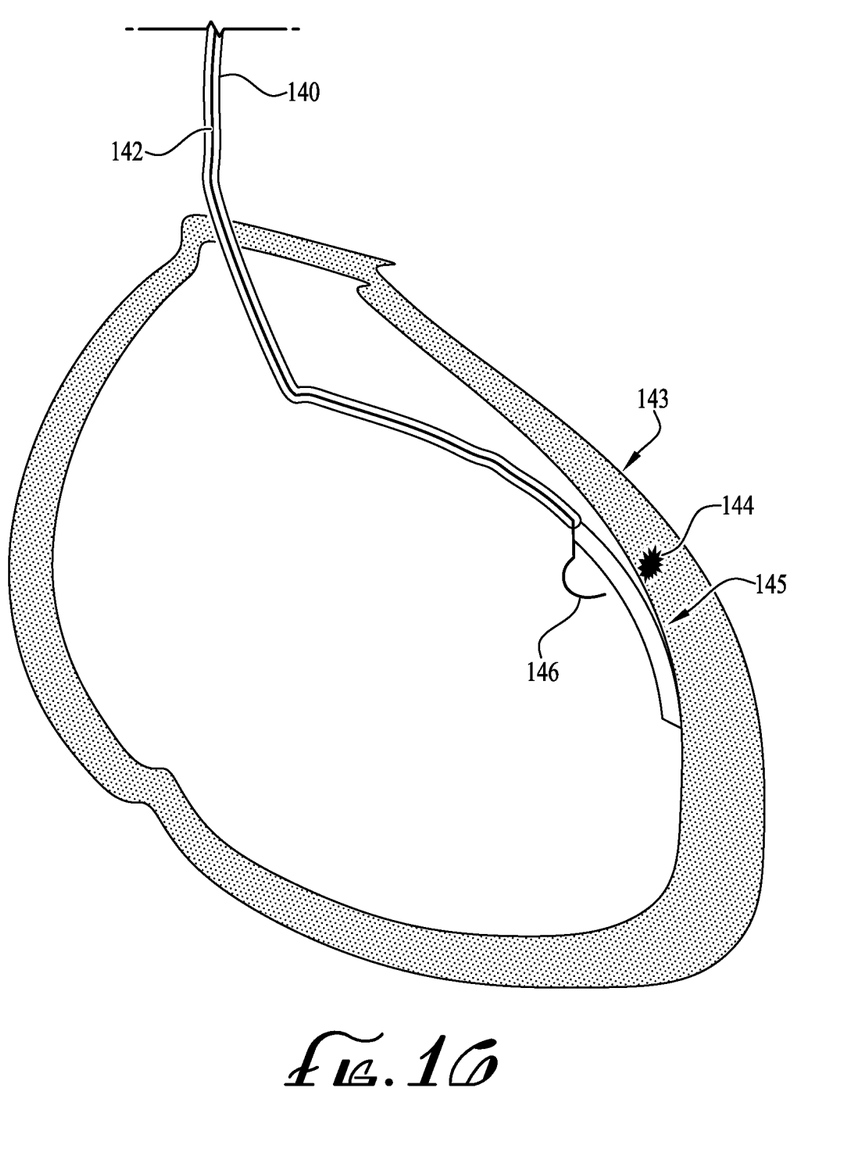
FIG. 16 shows the flexible 1-dimensional beta camera and detector-catheter incorporating features of the invention inside the ventricle of the heart with a separate injection catheter prior to injection, including ablation means.

FIG. 16 is another view of the 1-Dimensional beta camera 145 deployed in the heart 143 for detecting the radioactive tagged portions 144 thereof, and an integral injection needle 146 (or ablation device).

Figure 17A:
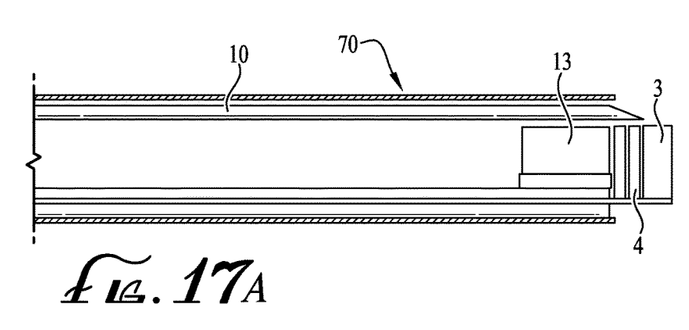
FIG. 17A is a cutaway side view of a detector-catheter that has radioactive markers 300 attached to its body so it can be seen by PET or gamma camera and correlate it with the location of the abnormal heart tissue.

FIG. 17A is a cutaway side view of a detector-catheter 70 that has radioactive markers 200, (see FIG. 17B) attached to its body so it can be seen by PET or gamma camera and correlate it with the location of the abnormal heart tissue.

Figure 17B:
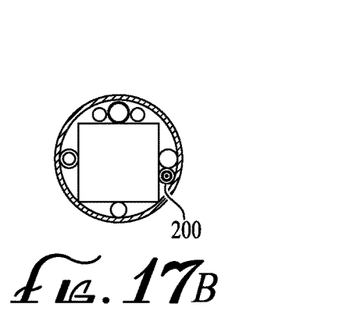
FIG. 17B is a cutaway end view of the catheter of FIG. 17A.

FIG. 17B is a cutaway end view of the catheter of FIG. 17A.

Figure 18A:
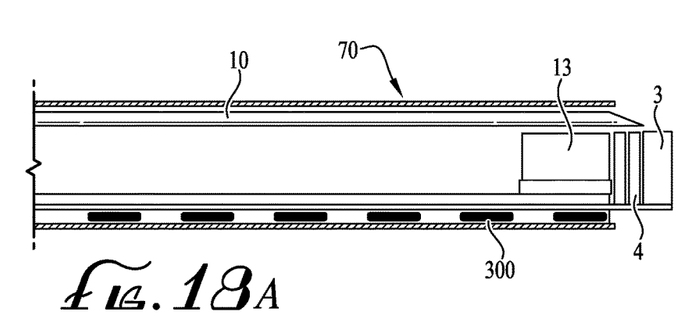
FIG. 18A is a further variation of the detector catheter of FIG. 17A detector catheter having and additional detector for optical, infra-red, or ultraviolet radiation.

FIG. 18A is a further variation of the detector catheter of FIG. 17A detector catheter having an additional detector 300 for optical, infra-red, or ultraviolet radiation.

Figure 18B:
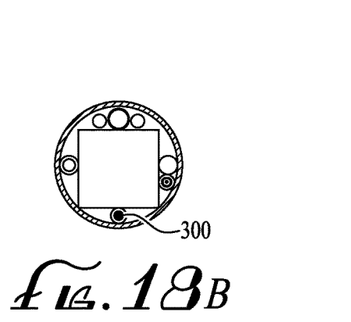
FIG. 18B is a cutaway end view of the catheter of FIG. 18A.

FIG. 18B is a cutaway end view of the catheter of FIG. 18A.

Figure 19:
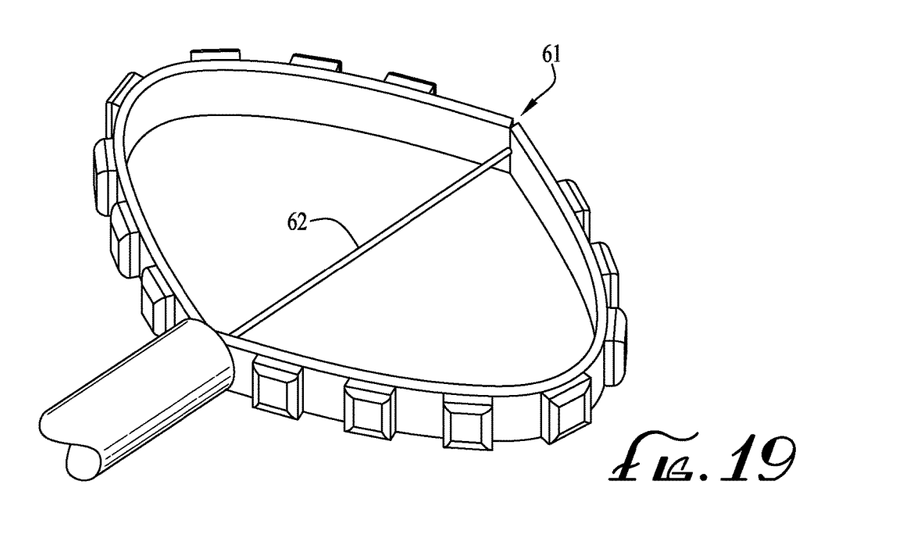
FIG. 19 is a further version of FIG. 12A showing the Beta camera formed on a flexible loop.

FIG. 19 is a further version of FIG. 12A showing the beta camera formed on a flexible loop. Two 1-Dimensional beta cameras similar to the one depicted in FIGS. 12A and B, are shown joined together to form a loop. The beta cameras 61 on the loop are pivoted around the central axis of the catheter when deployed in the heart. They are mounted on a flexible backing which can be bent to take the form of the myocardium inner wall by pulling on a cable 62 attached to the distal end of the flexible backing, the cable extending through the length of the placement catheter. The two portions of the loop of beta cameras each touch separate portions of the wall of the heart chamber to provide better apposition.

Described below are various novel methods for therapy using the catheters described herein based on real-time characterization of myocardial tissue utilizing radiopharmaceuticals.

Example 1

Evaluation of a Single-Detector Catheter in a Pig Heart with Infarct:

As an evaluation of the method and the instrument described and discussed in regard to FIG. 1, a flexible theranostic beta-detection catheter was constructed by coupling a 1×1 mm piece of plastic scintillator to a silicon photomultiplier and mounting the combination on a catheter as described below with flexible 60 cm long conduit extending the length of the catheter. The plastic scintillator was selected for its high efficiency positron detection and minimal gamma ray sensitivity, which reduces background signals and increases spatial resolution. A Tygon tube with outer diameter of 1.5 mm was also placed in the thin-walled catheter together with the detector and the flex circuit. The catheter tip also included a retractable 25 G needle for therapeutic delivery, which can be accessed via an attached injection port at the catheter base.

Myocardial infarctions (MI) were created in Yorkshire pigs (n=4) via 90 min balloon occlusions of the distal left circumflex arteries. Pigs were then injected with 0.5 mCi/kg 18FDG 1 week post-MI and sacrificed 90 min following injection. Hearts were imaged ex vivo via PET/CT. 18FDG signals of infarct/periinfarct zones were measured using the above described theranostic catheter and a gamma well counter.

Catheter-based endocardial measurements of 18FDG injected intramyocardially in biologically-relevant activities at depths of 1 mm in a bovine heart, have been demonstrated. The catheter device demonstrates a concentration-dependent relation to signal strength, recording values of 2 and 21 counts per second (CPS) for the 1 and 10 micro Ci samples, respectively. The sensitivity of the detector was 3000 CPS/micro Ci when in direct contact with a 1 mm$^2$ source of 18FDG. The difference in magnitude of signals detected in direct contact and in tissue (1 mm deep injections) reflects the limited range of 18F positrons in tissue (Rmax=2.4 mm). This contributes to high spatial resolution radiotracer detection to guide therapeutic delivery.

The beta-detection catheter registered consistently reproducible signals on the endocardial surface following post-MI injection of 18FDG. Myocardial sections containing infarct and peri-infarct tissue demonstrated heterogeneous 18FDG uptake at 1 week post-MI. Beta-detection catheter measurements show reasonable visual agreement with 18FDG PET/CT images and good visual and numerical correlation with gamma well counting data. The beta-detection catheter registered consistently reproducible signals on the endocardial surface following post-MI injection of 18FDG. Myocardial sections containing infarct and peri-infarct tissue demonstrated heterogeneous 18FDG uptake at 1 week post-MI.

In another procedure a post-MI patient was injected with F-18 labeled Annexin-V one or two hours prior to the procedure. Annexin-V accumulates in tissue that is undergoing apoptosis. The catheter includes at least one detector that is predominantly sensitive to positrons. After the area of myocardium that has highest uptake of Annexin-V is located using this detector, therapeutic compounds are injected into the myocardium. The injector can be an integral part of the detector catheter or a separate simultaneously positioned injector. Because the Annexin-V has accumulated in tissue that is undergoing apoptosis, the injected compound containing stem cells or angiogenic genes or factors can result in rehabilitation of the infarcted tissue, or the peri-infarcted tissue, and improve the heart's function.

Other radiolabeled compounds that are specific to infarcted or peri-infarcted tissue can also be used in this method. Alternatively, F-18 labeled FDG, which is attracted to health tissue, can be used and the probe will locate areas of the myocardium that has low or no FDG as areas of chronic infarction for injection with the therapeutic compound. Alternatively, F-18 FDG can be high in regions of acute reperfusion injury following myocardial infarction, or in other chronic inflammatory states like sarcoidosis or myocarditis. Once located, acute myocardial infarction can be treated with local therapies to promote repair and reduce adverse post-MI remodeling, including cell, gene and polymer therapies. In the cases of sarcoidosis or myocarditis the device can be used to direct a myocardial biopsy for diagnostic purposes.

Further, the therapeutic cells can be labeled with a radioactive isotope that emit gamma rays, such as Tc-99m. A few minutes after injection of these cells, a probe catheter can be used to verify the accumulation of these therapeutic cells in the myocardium and not into the blood pool. Another way to verify the intra-myocardial injection is to mix a colloidal radioactive solution into the therapeutic injectant. Alternatively, a fluorescent colloidal solution can be added to the injectant, and an appropriate light detector placed into the myocardium can be used to verify the implantation of the therapeutic cells or other materials into the appropriate tissues. This light detector can be a part of the original radioactive detector catheter or paced as a separate device. In the above method a detector catheter can be used that contains an electrode to examine the electrical signals of the heart tissue and further verify that the tissue that is being injected is infarcted or peri-infarcted tissue.

In another such method, the patient can be injected with a positron emitting labeled matrix metalloproteinase inhibitor that accumulates in the regions of the heart that are causing arrhythmia. Examples of this isotope include Ga-68, I-124, I-131, Re-186, Re-188, Cu-62 and Zr-89. Other radiolabeled compounds that have specific uptake characteristic to the abnormal tissue can also be used in this method.

Catheter incorporating features of the invention preferably contains at least one detector that is predominantly sensitive to beta rays. After locating the area of myocardium that has highest beta emitting uptake using the detector, a variety of local therapies can be administered.

As shown in the Figures, the injector for delivery of medicinal therapy can be an integral part of the detector-catheter. However, as discussed below and shown in FIG. 13 it is also contemplated that the injector can be a totally separate device that can be positioned separate from the sensing catheter.

A further example of medicinal therapy is the local delivery of a recombinant tissue inhibitor of matrix metalloproteinase-3 (TIMP-3), or a TIMP-3 releasing hydrogel, or activatable polymer that releases TIMP-3 in presence of MMP activity, activation leads to enhanced degradation of the polymer and release of TIMP-3 or other modulator of MMP activation TIMP-3 is known to moderate the proinflammatory status of macrophages. (Gill S E, Gharib S A, Bench E M, Sussman S W, Wang R T, Rims C, Birkland T P, Wang Y, Manicone A M and McGuire J K. "Tissue Inhibitor of Metalloproteinases-3 Moderates the Proinflammatory Status of Macrophages. *American Journal Of Respiratory Cell And Molecular Biology*. (2013); 49:768-777) and play a critical role in modulating post-MI remodeling. Eckhouse et al. have demonstrated that intramyocardial injection of TIMP-3 releasing hydrogel within the infarct region at the time of acute surgical-induced MI in pigs can reduce post-MI remodeling. (Eckhouse S R, Purcell B P, McGarvey J R, Lobb D, Logdon C B, Doviak H, O'Neill J W, Shuman J A, Novack C P, Zellars K N, Pettaway S, Black R A, Khakoo A, Lee T, Mukherjee R, Gorman J H, Gorman R C, Burdick J A and Spinale F G. "Local Hydrogel Release Of Recombinant TIMP-3 Attenuates Adverse Left Ventricular Remodeling After Experimental Myocardial Infarction", *Sci Transl Med*. (2014) 6:223ra21). These studies demonstrated an increase in wall thickness within the infarct region, a decrease in wall stress, and a reduction in LVEDV. The local and sustained release of recombinant TIMP-3 over several weeks from their MMP-activatable hydrogel resulted in a reduction in regional MMP activity, and a number of other inflammatory markers including; IL-8, MCP-1, and MIP-1α. (Eckhouse S R, Purcell B P, McGarvey J R, Lobb D, Logdon C B, Doviak H, O'Neill J W, Shuman J A, Novack C P, Zellars K N, Pettaway S, Black R A, Khakoo A, Lee T, Mukherjee R, Gorman J H, Gorman R C, Burdick J A and Spinale F G. "Local Hydrogel Release of Recombinant TIMP-3 Attenuates Adverse Left Ventricular Remodeling After Experimental Myocardial Infarction". *Sci Transl Med*. (2014) 6:223ra21).

The methods discussed herein can be performed while the patient is undergoing a PET scan or a gamma camera scan. These external imaging modalities can facilitate accurate localization and delivery of therapy. For example, in one embodiment, the catheters include radioactive or radiopaque markers at their tip or along their axis (FIGS. 18A, 18B) so they can be seen in the external images, and enable correlation with the radiolabeled tissues. In another embodiment, the catheters can contain position trackers at their tip or along their axis so they can be correlated with their location in the external images, and enable correlation with the radiolabeled tissues.

With reference to FIG. 16, various non-drug therapies that can be delivered in conjunction with the label sensing catheter described herein are radiofrequency ablation or cryo-ablation, which are current methods of therapy for arrhythmias. In one embodiment of the detector-catheters of this invention, electrodes are utilized to examine the electrical signals of the heart tissue as well as the radioactive distribution.

In another embodiment, the catheter can also contain position sensors for tracking. In one method of use, the ablation catheters are guided to the abnormal tissue location using the detector-catheter. Alternatively, structure for delivering the radiofrequency or cryoablation can be incorporated into the detector-catheter.

Theranostic catheters developed for both radiation detection and molecularly-targeted therapeutic injection as shown in the Figures. The diameter of the flexible catheter is 2.4 mm. The detector on the catheter tip consists of a plastic scintillators (BC-412, St. Gaubain, Fr) coupled to a 1 mm×1 mm solid state photomultiplier (MPPC Hamamatsu Photonics, Japan). The plastic scintillator was selected for its high efficiency detection of beta rays and minimal sensitivity to gamma rays, which reduces signals from background radiation and increases spatial resolution. The catheter also includes a retractable 25 G needle for therapeutic delivery, which can be accessed via an injection port on the catheter base. Basic feasibility experiments were conducted to assess the prototype device's sensitivity and ability to measure signals from intramyocardial beta-emitting radiotracers. Fifty (50) L quantities of serially diluted aqueous 18FDG were injected locally into sections of an ex vivo pig heart at depths of 1 mm from the endocardial surface. 18FDG signals were assessed by collecting counts with the catheter tip in direct endocardial contact.

Example 2

A multi-detector catheter (see FIG. 19) similar to basket-shaped catheters used in electrophysiology studies, which will reduce the time needed for intraventricular mapping of radionuclide detection by incorporating multiple detectors on a single catheter that can be deployed to provide direct contact with the endocardial surface of the heart.

The detector on the tip of the catheters shown in the Figures consists of a plastic scintillator (BC-412, St. Gaugin, France) coupled to a 1 mm×1 mm Si photodiode (Hamamatsu Photonics, Japan). The theranostic catheter developed for both beta detection and targeted therapeutic delivery is shown in the FIGS. 1A, 1B. The diameter of the flexible catheter is 2.4 mm. The prototype catheter was shortened significantly for simplicity; a longer catheter is required for percutaneous arterial access to the heart. The catheter tip also features a retractable 25 G needle for therapeutic delivery, which can be accessed via an injection port on the catheter base. A guidewire system is added to this catheter as well to facilitate placement within the left ventricle.

The detector portion of the catheter described can include both beta and gamma detectors (FIGS. 2A, 2B), to more effectively isolate beta particles from background gamma emissions. In variations of the systems described in vivo mapping is provided by the addition of an electrode for detection of electrical activity. A multi detector system can be provided by using several solid-state photomultipliers (such as 8 SSPMs) attached to a flexible Kapton printed circuit board (1 mm wide and 40 mm long) (FIG. 15). These SSPM's are 1×1 mm in dimension and each are coupled to 1.5×1.5 mm piece of plastic scintillator.

In summary, described herein are various novel methods for locating labeled tissue within the body and delivering therapy to the labeled tissue based on real-time characterization of myocardial tissue. Radiopharmaceuticals, fluorescing materials and other known techniques and materials can be used to tag the target tissue. The catheters described therein are then used to locate the tagged tissue and deliver and inject into the target tissue a treatment modality including, but no limited to—cells, genes, polymers, inhibitory microRNAs, DNA, plasmids, chemicals, enzymes, growth factors, or a variety of medicinal compounds or combinations thereof.

In the methods described herein a detector catheter can be used that contains an electrode to examine the electrical signals of the heart tissue and further verify that the tissue that is being injected into is infarcted or peri-infarcted tissue.

Another therapy is the use of radiofrequency ablation alone or in combination with directly delivered drug therapy. A detector catheter can be used that contains electrodes to examine the electrical signals of the heart tissue and to then deliver electrical energy for ablation.

The methods discussed above can be performed under a PET scanner of a gamma camera. These external imaging modalities can further facilitate accurate localization and delivery of therapy.

The catheters can also include radioactive or radiopaque markers at their tip or along their axis so they can be seen by external imaging devices, and enable correlation with the position of the radiolabeled/tagged tissues.

We claim:

1. A catheter for locating and treating tagged tissue within a human body comprising:
    a tube steerable through a vessel within the human body, said tube including in or on a distal end thereof one or more detectors for locating labeled tissue within the human body,
    a lumen extending from a proximal end of said tube to the distal end of said tube, and
    a retractable and extendable needle positioned in said lumen adjacent the distal end of said tube, said needle having a hollow conduit attached thereto and extending through said lumen to the proximal end of said tube, the hollow conduit configured to provide a treatment modality.

2. The catheter of claim 1 wherein the one or more detectors detects beta-rays, gammas rays, xrays, fluorescence, or electrical activity.

3. The catheter of claim 2 further including a CCD camera in or on a distal portion of the catheter.

4. The catheter of claim 2 further including one or more of a laser, electrodes for sensing electrical signals from the heart and a biopsy needle.

5. The catheter of claim 1 wherein the treatment modality comprises a liquid comprising cells, genes, polymers, inhibitory microRNAs, DNA, plasmids, chemicals, enzymes, growth factors, medicinal compounds or combinations thereof.

6. The catheter of claim 1 wherein the treatment modality comprises delivery electrical energy or provides tissue ablation.

7. The catheter of claim 1 further including a location indicator in or on a distal portion of the catheter.

8. The catheter of claim 7 wherein the location indicator is a signal transmitting position sensor.

9. The catheter of claim 7 wherein the location indicator comprises radiopaque makers.

* * * * *